United States Patent
Barry et al.

[19]

[11] Patent Number: 5,911,710
[45] Date of Patent: Jun. 15, 1999

[54] MEDICAL INSERTION DEVICE WITH HEMOSTATIC VALVE

[75] Inventors: Robert Barry, Kirkland, Wash.; Theodore Lamson, Saratoga Springs, N.Y.; Gregory Lambrecht, Cos Cob, Conn.; Michael Gertner, West Long Branch, N.J.

[73] Assignee: Schneider/Namic, Glens Fall, N.Y.

[21] Appl. No.: 08/850,265

[22] Filed: May 3, 1997

[51] Int. Cl.⁶ ....................................................... A61M 5/00
[52] U.S. Cl. ........................... 604/249; 604/537; 604/167
[58] Field of Search ..................................... 604/246, 249, 604/256, 283, 164, 167, 169

[56] References Cited

U.S. PATENT DOCUMENTS

| | | |
|---|---|---|
| 4,430,081 | 2/1984 | Timmermans . |
| 4,580,573 | 4/1986 | Quinn . |
| 4,626,245 | 12/1986 | Weinstein . |
| 4,857,062 | 8/1989 | Russell . |
| 4,895,346 | 1/1990 | Steigerwald . |
| 4,929,235 | 5/1990 | Merry et al. . |
| 4,978,341 | 12/1990 | Niederhauser . |
| 4,978,344 | 12/1990 | Dombrowski et al. . |
| 5,000,745 | 3/1991 | Guest et al. . |
| 5,006,114 | 4/1991 | Rogers et al. . |
| 5,041,095 | 8/1991 | Littrell . |
| 5,051,109 | 9/1991 | Simon . |
| 5,092,845 | 3/1992 | Chang . |
| 5,092,846 | 3/1992 | Nishijima et al. . |
| 5,098,406 | 3/1992 | Sawyer . |
| 5,102,395 | 4/1992 | Cheer et al. . |
| 5,106,054 | 4/1992 | Mollenauer et al. . |
| 5,114,408 | 5/1992 | Fleischhaker et al. . |
| 5,125,903 | 6/1992 | McLaughlin et al. . |
| 5,127,626 | 7/1992 | Hilal et al. . |
| 5,154,701 | 10/1992 | Cheer et al. . |
| 5,167,637 | 12/1992 | Okada et al. . |
| 5,176,652 | 1/1993 | Littrell . |
| 5,195,980 | 3/1993 | Catlin . |
| 5,205,829 | 4/1993 | Lituchy . |
| 5,207,649 | 5/1993 | Aruny . |
| 5,215,527 | 6/1993 | Beck et al. . |
| 5,215,528 | 6/1993 | Purdy et al. . |
| 5,256,150 | 10/1993 | Quiachon et al. . |
| 5,267,966 | 12/1993 | Paul . |
| 5,269,997 | 12/1993 | Vetter et al. . |
| 5,273,546 | 12/1993 | McLaughlin et al. . |
| 5,290,245 | 3/1994 | Dennis . |
| 5,290,249 | 3/1994 | Foster et al. . |
| 5,300,033 | 4/1994 | Miller . |
| 5,304,142 | 4/1994 | Liebl et al. . |
| 5,304,143 | 4/1994 | Green et al. . |
| 5,304,156 | 4/1994 | Sylvanowicz et al. . |
| 5,312,362 | 5/1994 | Pfolsgraf et al. . |
| 5,312,363 | 5/1994 | Ryan et al. . |
| 5,330,436 | 7/1994 | Heidmueller . |
| 5,334,160 | 8/1994 | Ellis . |
| 5,336,192 | 8/1994 | Palestrant . |
| 5,350,362 | 9/1994 | Stouder, Jr. . |
| 5,350,363 | 9/1994 | Goode et al. . |
| 5,356,390 | 10/1994 | Erskine . |
| 5,366,446 | 11/1994 | Tal et al. . |
| 5,403,292 | 4/1995 | Ju . |
| 5,458,640 | 10/1995 | Gerrone .................................. 604/264 |
| 5,584,808 | 12/1996 | Healy ........................................ 604/86 |
| 5,591,137 | 1/1997 | Stevens . |
| 5,599,305 | 2/1997 | Hermann et al. .......................... 604/95 |

*Primary Examiner*—Corrine McDermott
*Attorney, Agent, or Firm*—Kenyon & Kenyon

[57] ABSTRACT

A medical insertion device that reduces the drag force exerted on an elongated member such as a catheter that is inserted through the device, increases maneuverability of the elongated member throughout the procedure in which the device is used and provides hemostasis. The device comprises a sheath housing and shuttle housing; the shuttle housing moves relative to the sheath housing. An elastomeric valve that contains an openable radial slit is provided in the sheath housing and provides hemostasis until the shuttle housing is biased towards the sheath housing. When the shuttle housing is biased forward, a generally tubular shuttle tube in the shuttle housing opens the slit in the elastomeric valve. The device is constructed so that, within the shuttle housing, hemostasis is provided after the shuttle tube has biased the elastomeric valve open.

17 Claims, 10 Drawing Sheets

MEDICAL INSERTION DEVICE WITH HEMOSTATIC VALVE

BACKGROUND OF THE INVENTION

This invention relates to medical insertion devices generally and in particular to devices that are designed to facilitate introduction of elongated members such as catheters into a vascular system, improve maneuverability throughout the vascular system and provide hemostasis.

Typically, catheter introducers that are presently available have a sheath tube attached to a distal end which is inserted into an artery of a patient, thus providing a user such as a physician with access to the vascular system. The proximal end of such introducers provides an opening for insertion of a catheter through the device into a patient's vascular system. The sheath tube is in fluid communication with an interior passageway of the introducer and the proximal end of the introducer, so that a catheter may be inserted through the device and into the artery. Once the distal end of the tube is inserted into the vasculature, blood can flow into the catheter introducer because the sheath tube is in fluid communication with the patient's bloodstream. Thus, blood also can flow through the catheter introducer and out of the proximal end of the device.

Controlling the blood loss is extremely important since blood loss endangers and traumatizes the patient and risks exposing the attendant user to blood-borne pathogens and diseases. The flow of blood from a catheter introducer also hinders a user's ability to manipulate the catheter. Thus, catheter introducers have been equipped with normally-closed elastomeric valves designed to maintain hemostasis after the distal end of the introducer is inserted into the vascular system of a patient.

Elastomeric valves that have been used in catheter introducers typically have a slit that normally is closed, so that when there is no catheter or guide wire present in the device the valve presents a sealed face to the blood flow from the patient. The slit permits the insertion of a catheter or guide wire therethrough and thus permits access to the patient's vascular system. The valve is designed typically so that the valve engages the periphery of the catheter or guide wire to seal the system and maintain hemostasis.

In order to maintain hemostasis, these slit valve designs must be biased such that they are closed when no catheter is present and must also be biased such that they seal around a catheter when present. A consequence of such designs is that the user must overcome the frictional force that results from the valve being biased closed in order to insert a catheter through the valve. Since catheters have very small diameters, particularly when compared to their length, kinking of the catheter can occur if the frictional forces that must be overcome are too great. Moreover, advancing a catheter through the vascular system of a patient, including advancement through the aortic arch of a patient, frequently requires subtle manipulations so that the catheter is advanced to the proper destination without damaging vascular tissue. Where advancement of a catheter through a catheter introducer requires overcoming large frictional forces, the difficulty of manipulating the catheter in a subtle manner can be greatly increased, thereby increasing the risk of injury to the patient.

Thus, there exists a need to provide a catheter introducer that maintains hemostasis after inserting a catheter into the vascular system of a patient while reducing the frictional forces on catheters inserted into the introducer.

This need also exists with respect to other types of medical insertion devices, such as Y-adapters and tri-adapters. These devices typically are used with elongated members of various sizes, such as are used in interventional procedures, such as angioplasty and stent implantation. In such procedures, members of various sizes, such as balloon catheters and stents, are inserted through the device and into the vasculature.

SUMMARY OF THE INVENTION

The present invention comprises a medical insertion device that introduces an elongated member such as a catheter into a vascular system and facilitates maneuverability of the elongated member through the vascular system while providing hemostasis. The medical insertion device according to this invention comprises a housing, an elastomeric valve, a shuttle tube, and a means for maintaining hemostasis. The housing has proximal and distal ends and an interior lumen extending through the housing. The elastomeric valve is secured within the interior lumen of the housing and preferably is constructed with an openable slit extending through the valve. The shuttle tube has proximal and distal ends and an interior passageway extending through it, is movable, and is constructed to bias the elastomeric valve open when moved to a forward position. The shuttle tube is located within the interior lumen of the housing, and the interior passageway is in fluid communication with the interior lumen of the housing.

The means for maintaining hemostasis may comprise structures such as a fluid bearing or washer valve. In general, any means which can form a fluid-tight seal around the periphery of a member to be inserted in the housing may be employed.

DETAILED DESCRIPTION OF THE PREFERRED EMBODIMENTS

The invention utilizes a valve and a separate means for maintaining hemostasis in order to provide hemostasis while significantly reducing the frictional forces on catheters, guide wires and other members inserted through the device. The valve preferably is a normally closed elastomeric valve, and provides hemostasis around, or in the absence of, catheters and other elongated members. The separate means maintains hemostasis when the first valve is biased open.

The devices of the invention also provide the ability to vary the drag force exerted upon a catheter or other member inserted through the device. By providing two different structures that can exert different drag forces upon the member, the physician may vary the level of maneuverability. If the physician desires greater maneuverability, the physician may use the means for maintaining hemostasis as the primary or sole provider of hemostasis, which exerts a lower drag force than the valve. However, if maneuverability is not a major concern during an aspect of a procedure, the user may employ the valve as the primary or sole provider of hemostasis.

Figure 1:
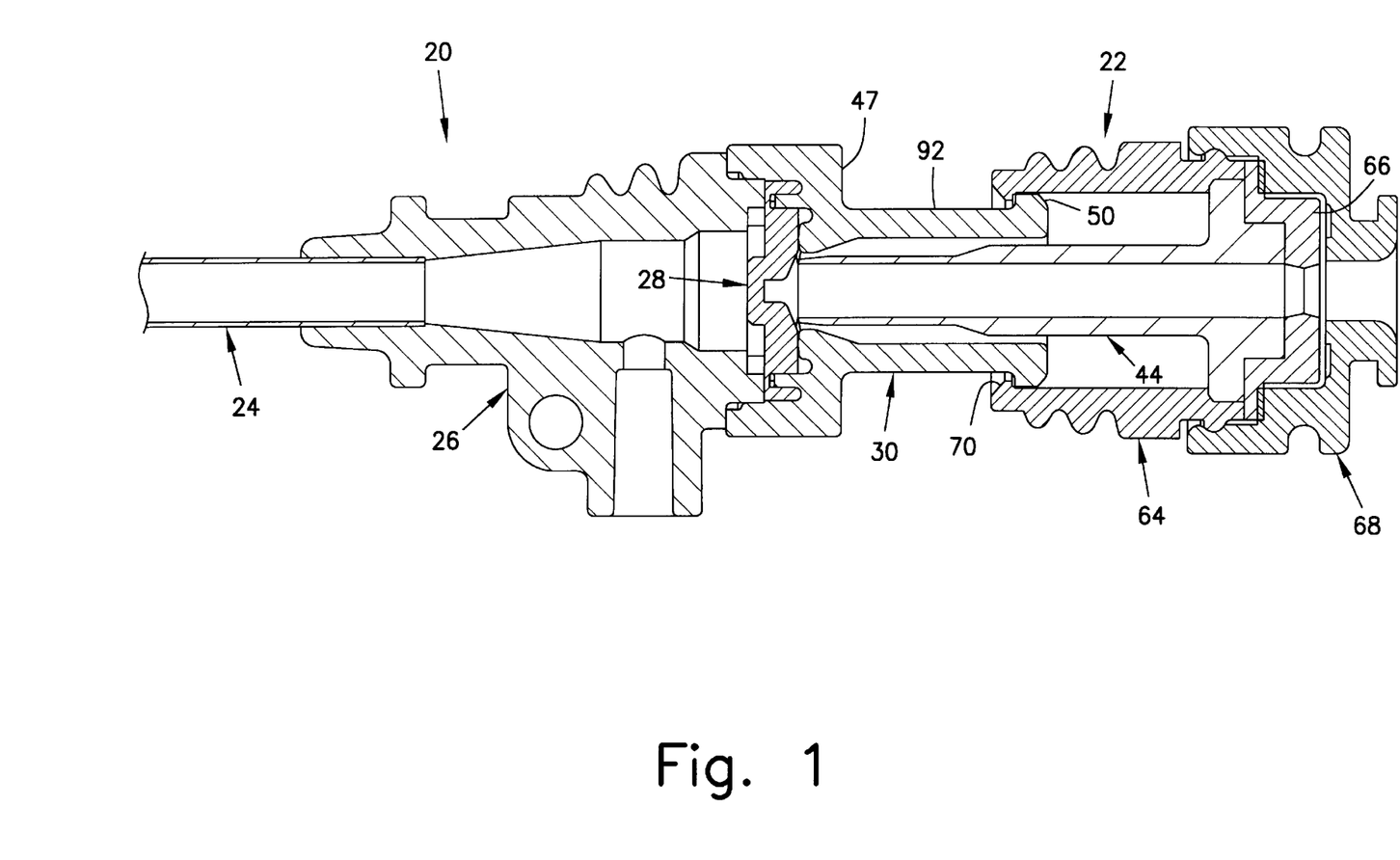
FIG. 1 is a longitudinal cross-sectional view of a catheter introducer of the invention, with the sheath valve in a closed position.

As illustrated in FIG. 1, a device of the invention may comprise two housings: a sheath housing 20 and a shuttle housing 22. The sheath housing contains a sheath valve 28, which can be biased open by shuttle tube 44 of the shuttle housing to reduce the frictional forces on a catheter inserted through the sheath valve. Means for maintaining hemostasis, preferably in the form of a shuttle valve 66, positioned in the shuttle housing, can serve to maintain hemostasis when the sheath valve 28 is biased open by shuttle tube 44 (and thus is not sealed around a catheter), by sealing around the periphery of a catheter inserted in the introducer.

Figure 2:
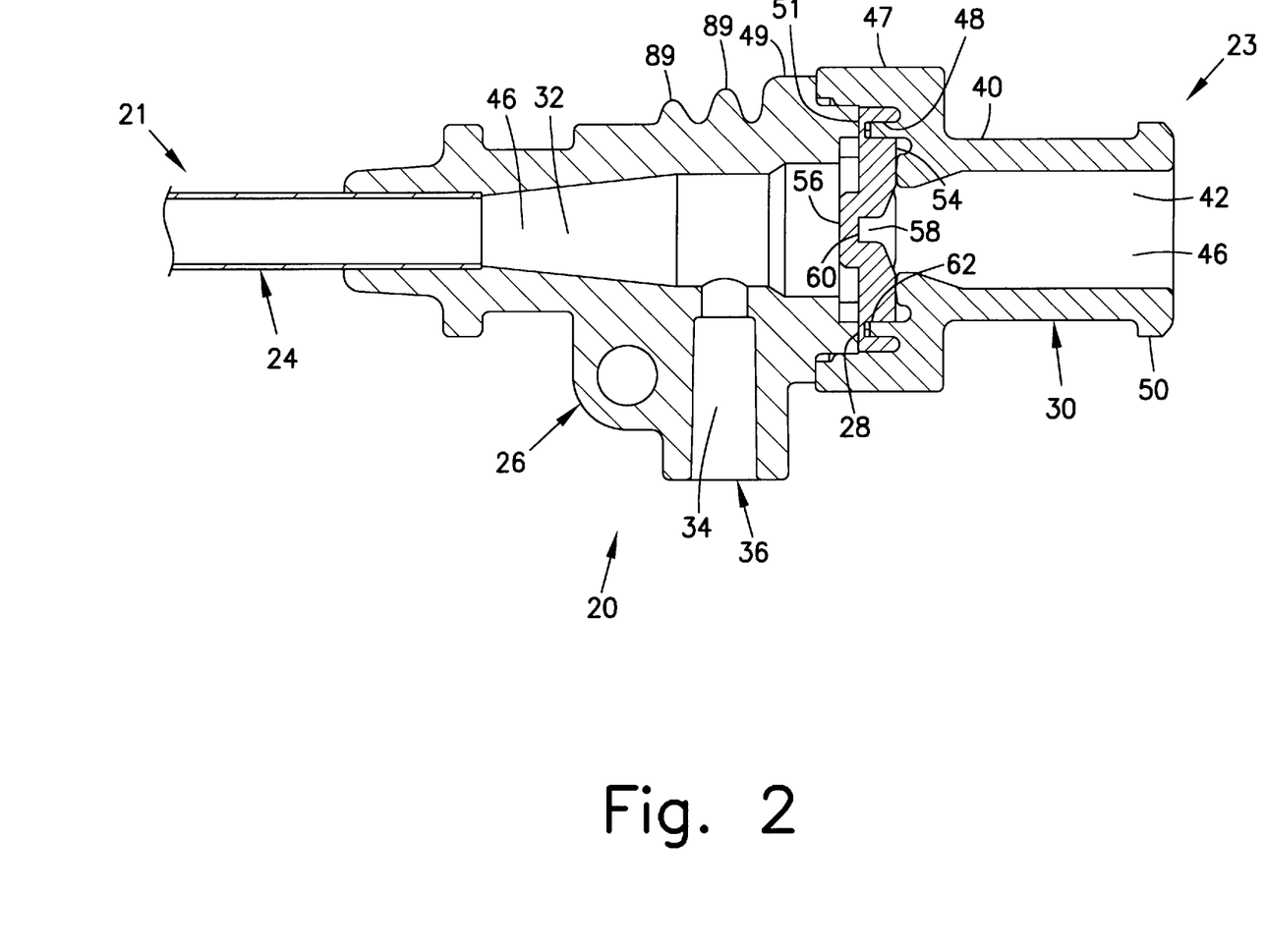
FIG. 2 is a longitudinal cross-sectional view of the sheath housing of the catheter introducer of FIG. 1.

As can be seen in FIG. 2, the sheath housing 20 has a distal end 21 and a proximal end 23. The sheath housing 20 preferably comprises a sheath tube 24, a sheath hub 26, a sheath valve 28, and a sheath cap 30.

Sheath hub 26 has an interior passageway 32, which extends from distal end 21 of the sheath housing 20 to the sheath valve 28 located at the proximal end of sheath hub 26. The sheath hub 26 preferably is composed of a relatively rigid, biocompatible material. Preferred materials for the sheath hub 26 are polymeric materials such as Pebax®, which is a biocompatible polyether block amide sold by Atochem, and Isoplast®, which is a biocompatible polyurethane sold by Dow Chemical Company.

The diameter of passageway 32 is larger near the sheath valve 28 than at the distal end of the passageway. This gradual taper can serve several purposes. In cardiological procedures, physicians sometimes utilize catheters which have curved distal ends, such as pigtail catheters. A gradual taper of passageway 32 can provide a transition area for entry of the curved end of such a catheter toward the sheath tube. A relatively larger space near the sheath valve 28 can provide an area into which sheath valve 28 can expand. The ability of sheath valve 28 to readily expand can decrease the drag force exerted on members inserted therethrough.

Sheath tube 24 is preferably insert molded to a surface which defines the interior passageway 32, and which extends out of the distal end 21 of the sheath hub 26. However, sheath tube 24 may be affixed to the interior passageway 32 by any other suitable means, such as welding, bonding or gluing. Sheath tube 24 preferably is composed of a relatively rigid, biocompatible material. Pebax® is particularly preferred for sheath tube 24. The distal end of the sheath tube 24 is adapted for insertion into a patient's artery (not shown). Thus, when sheath tube 24 is inserted into an artery of a patient, fluid communication is established between a patient's bloodstream and the interior passageway 32 of the sheath hub 26.

A side passageway 34 preferably is in fluid communication with, and extends from, interior passageway 32 to a sheath port 36. Since side passageway 34 is in fluid communication with interior passageway 32, which is itself in fluid communication with sheath tube 24, fluids such as contrast or imaging agent may be injected through the sheath port 36 into a patient's bloodstream. Saline solution may also be injected into port 36 to flush the interior passageway 32 and reduce the incidence of blood clotting. A stopcock (not shown) can be attached to port 36, to maintain the port in a closed position when the port is not being accessed to flush the passageway 32 or inject fluids into a patient's bloodstream.

Ridges 89 are located on the outer surface of the sheath hub 26, and can provide a better grip for the user. If the sheath hub 26 is injection-molded, the ridges 89 also help provide a uniform thickness to the hub.

The proximal end of hub 26 preferably contains a shoulder 49, constructed to abut an outer shoulder 47 of sheath cap 30. Annular section 51, which projects axially beyond shoulder 49, is constructed to contact sheath valve 28 to maintain it in place between hub 26 and cap 30.

Sheath cap 30 preferably comprises an outer shoulder 47 and a sheath cap body 40 and a collar 50, which most preferably are formed as a unitary element, such as by injection or compression molding. Sheath cap 30 preferably is composed of a relatively rigid, biocompatible material. Preferred materials for the sheath cap 30 are polymeric materials such as Isoplast®. The collar 50 is located at the proximal end of the sheath cap 30, which is preferably constructed to be snap fitted to a corresponding rim 70 of the shuttle housing 22. (See FIG. 1). The design of the sheath cap 30 preferably is the same for Y- and tri-adapters.

The sheath cap body 40 preferably is a generally cylindrical body having an interior passageway 42 extending from the proximal end 23 of sheath housing 20 to the proximal side of sheath valve 28. Interior passageway 42 preferably tapers inwardly toward the distal end of the sheath cap 30. The diameter of passageway 42 should be large enough, even in the tapered portion, to receive shuttle tube 44 of the shuttle housing when it is biased into interior passageway 42. (See FIG. 4). The interior passageway 42 preferably is axially aligned with the interior passageway 32 of the sheath hub 26, and together they form sheath lumen 46, so that a catheter or guide wire inserted into the proximal end 23 of sheath housing 20 may be axially advanced to the distal end 21 of housing 20, and into a patient's vascular system.

An annular ring 48 is preferably is located inside the outer shoulder 47, with an annular gap therebetween. Preferably, outer shoulder 47 extends axially beyond the length of annular ring 48. The inner surface of the outer shoulder 47 is attached to the outer surface of annular section 51.

Sheath valve 28 preferably includes a base flange 54 and a disc 56, which has a slit 60 therein. Slit 60 is normally closed, and is constructed to receive a catheter or guide wire inserted therethrough. Any suitable valve design that is normally closed to maintain hemostasis around, or in the absence of, a catheter or guide wire can be employed with the invention. Likewise, the slit can be a single slit, or multiple slits of any suitable size and design. Optionally, the disc 56 can have a pilot opening 58 on its proximal face, so that the slit 60 extends from the distal end of the pilot opening to the distal face of the disc. Sheath valve 28 also can be a multi-piece construction, such that, for example, one component has a pilot opening and a second component adjacent the first component has a slit therethrough. However, a unitary construction is preferred. The preferred valve design includes a pilot opening and a single slit extending radially across the center of the distal face of the valve, and extending into the valve body to meet the distal end of the pilot opening.

Sheath valve 28 preferably is secured between hub 26 and cap 30. Thus, hub 26 and cap 30 can be fabricated separately, and then joined together with valve 28 therebetween. However, it is not essential that these components be fabricated separately. In embodiments where valve 28 is secured between hub 26 and cap 30, as is shown in FIG. 1, hub 26 and cap 30 can be secured together by any suitable means. It is particularly preferred that hub 26 and cap 30 are ultrasonically welded together.

Annular recess 62 on the valve base flange 54 is engaged by the annular ring 48 on the outer shoulder 47, to assist in securing sheath valve 28 in place. Thus, sheath valve 28 can be secured in a nesting relationship between cap 30 and hub 26 to provide added stability.

Valve 28 preferably is composed of an elastomeric material such as silicone. The preferred material for valve 28 is Med-4035, a silicone elastomer sold by Nusil. The preferred material has a durometer of about 35. Preferably, silicone materials having a durometer of about 20 to 80 are used with the invention. The thickness of valve 28 can vary depending on the particular needs of the user. Since shuttle tube 44 can bias valve 28 open prior to inserting a catheter or guide wire therethrough, as discussed in more detail below, valve 28 can be somewhat thicker than might otherwise be desirable if the user were required to overcome the frictional forces of the valve by inserting a catheter or guide wire through the slit. Thus, if a somewhat thicker valve is used, it will be easier to maintain hemostasis, and the fluid pressure at which the seal will fail will be higher. In general, valve thicknesses of about 0.050 to 0.150 inches are preferred, and a thickness of about 0.085 inches is most preferred.

Figure 3:
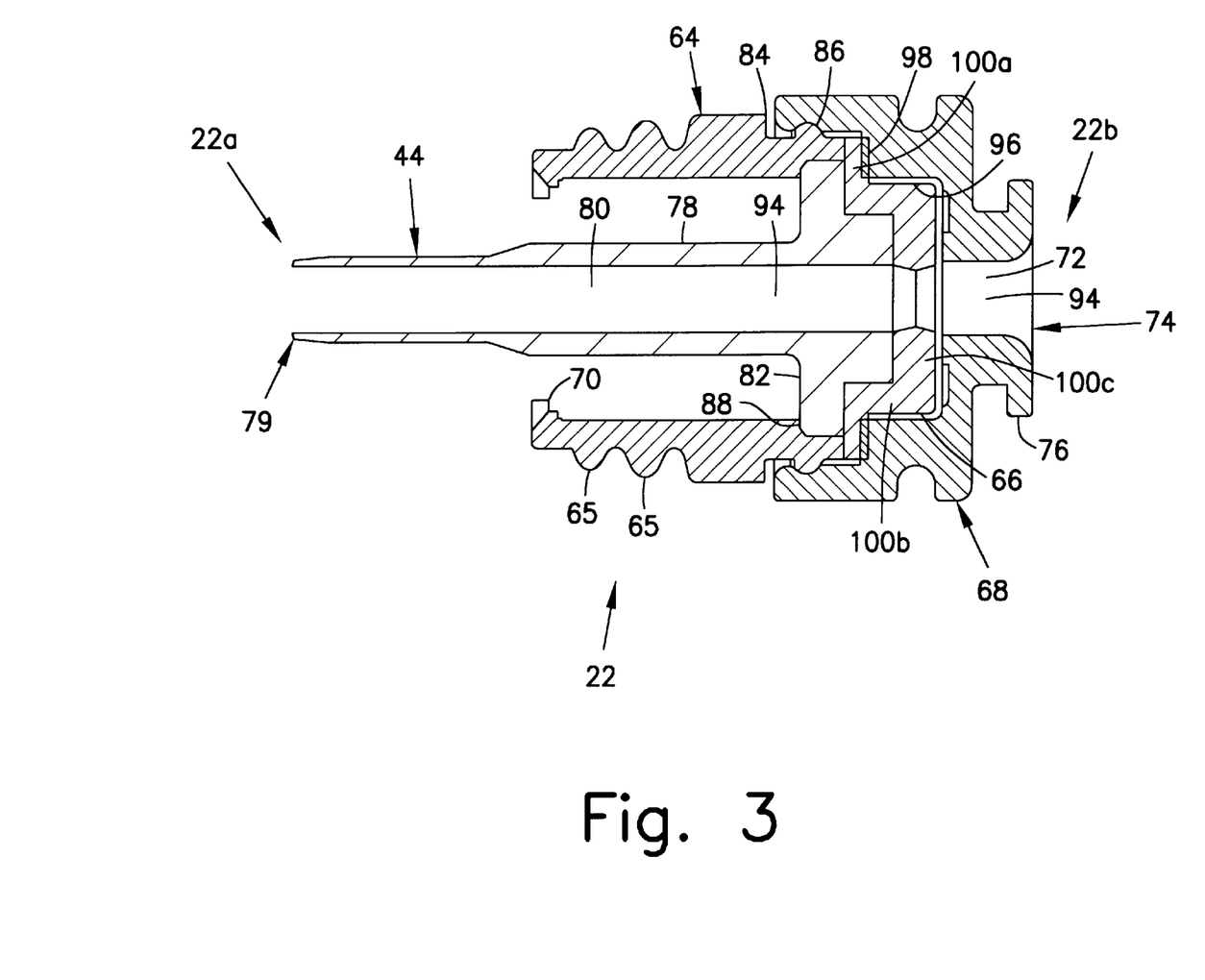
FIG. 3 is a longitudinal cross-sectional view of the shuttle housing of the catheter introducer of FIG. 1.

As shown in FIG. 3, the shuttle housing 22 has a distal end 22a and a proximal end 22b. Housing 22 preferably comprises a shuttle body 64, a shuttle valve 66, a shuttle cap 68, and a shuttle tube 44. Shuttle body 64 has a proximal and distal end, and preferably is generally tubular-shaped, with ribs 65 provided on its outer surface. A rim 70 is located at the distal end of the shuttle body 64 and fastens the shuttle housing 22 to the sheath housing 20 (see FIG. 1). The shuttle body 64 preferably is composed of a relatively rigid, biocompatible material. Preferred materials for the shuttle body 64 are polymeric materials such as Isoplast® or polypropylene.

The shuttle cap 68 has a proximal and distal end, preferably is generally symmetrical about a longitudinal center axis and contains a central passageway 72. An entrance port 74 is located at the proximal end of the shuttle cap to provide an entry location for a catheter or guide wire. Central passageway 72 preferably tapers outwardly towards the entrance port 74 to facilitate insertion of a member such as a catheter. An annular ring 76 is located on the proximal end of cap 68 and can function as a peripheral flange that can receive external devices such as a dilator (not shown) by a snap fit over the ring 76. Cap 68 also contains a shuttle cap rim 84 at its distal end, which is adapted to engage a rib 86 on the shuttle body 64 to snap fit the cap and shuttle body. Cap rim 84 preferably is a circumferential lip extending radially inwardly at the distal end of cap 68. Rim 84 should extend radially inwardly a sufficient distance so that rib 86 extends outwardly beyond the innermost point of rim 84.

Thus, rim 84 is retained in place by rib 86. Rim 84 can be rounded at its end to facilitate a snap fit construction. Likewise, rib 86 can have a slightly chamfered construction to facilitate sliding rim 84 over the rib to snap fit cap 68 and shuttle housing 64. Preferably, the distal side of rib 86 is flat to engage rim 84 such that cap 68 and housing 64 are not readily disassembled once snap-fitted together.

Cap 68 preferably is formed of a relatively rigid polymeric material and preferably is more rigid than the other polymeric components of the catheter introducer. The most preferred material for cap 68 is polypropylene.

Shuttle tube 44 preferably is a unitary element, and should be composed of a relatively rigid material such as polypropylene. Shuttle tube 44 includes a generally tubular section 78, which has an interior passageway 80. Shuttle tube 44 preferably comprises a series of flattened and curved surfaces along its longitudinal axis. The flattened surfaces can help prevent blood clotting in the interior passageway 32 of the sheath hub 26, and in the interior passageway 42 of the sheath cap 30.

Figure 4:
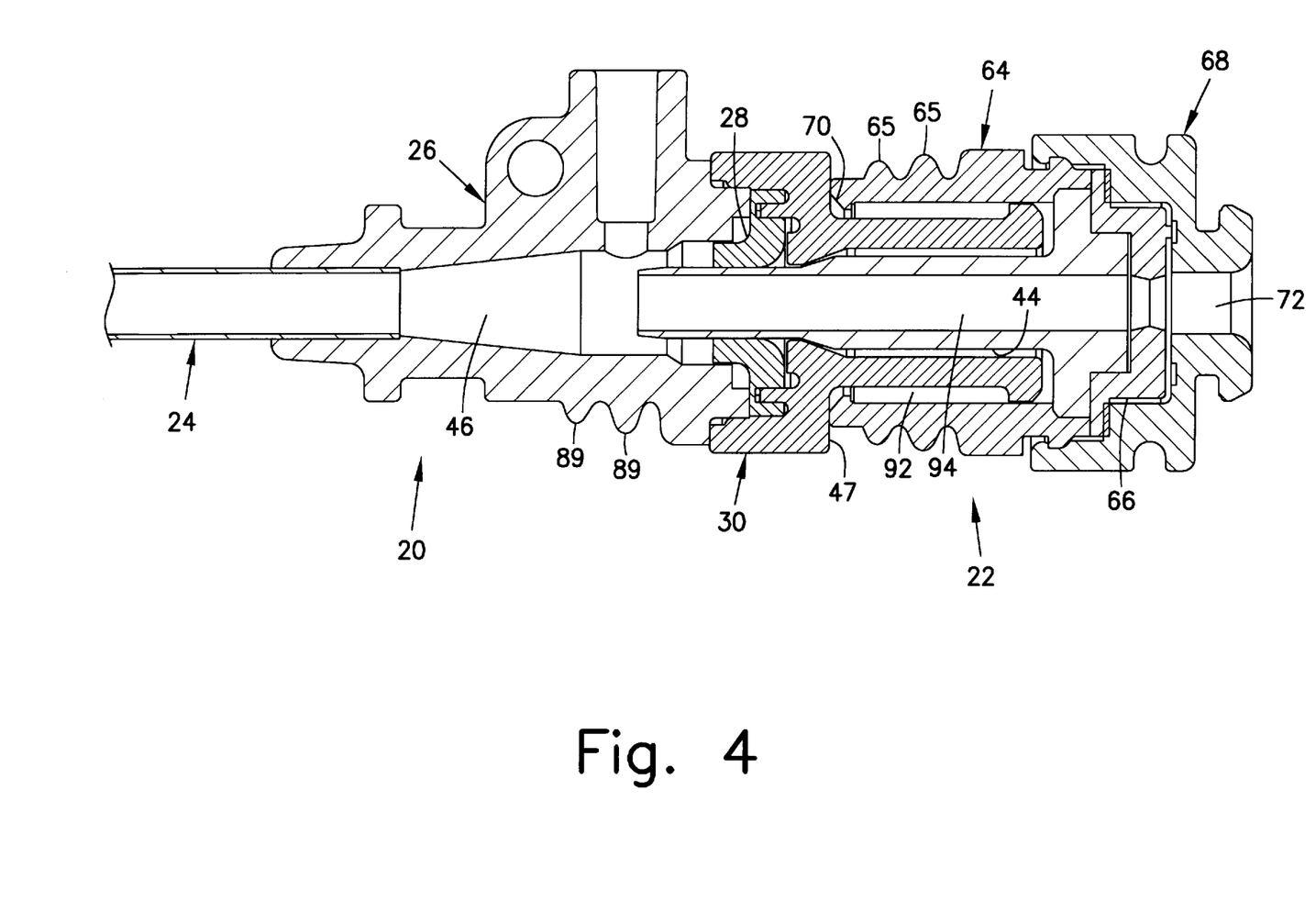
FIG. 4 is a longitudinal cross-sectional view of the catheter introducer of FIG. 1, with the sheath valve in an open position.

The inner diameter of the tubular section 78 should be slightly larger than the diameter of a catheter to be passed through it. A shoulder flange 82 preferably is located near the proximal end of shuttle tube 44 to assist in securing shuttle valve 66, which is discussed in more detail below. The distal tip 79 of shuttle tube 44 preferably tapers inwardly, which can help facilitate opening the sheath valve 28. The distal portion of the shuttle tube 44 is also preferably thinner than the proximal portion of the shuttle tube; as shown in FIG. 4, the change in thickness allows a gap to be formed between the shuttle tube and inner surface of the sheath cap 30 when the shuttle tube 44 is biased forward. This gap allows any blood that may have seeped between the sheath valve 28 and shuttle tube 44 to flow into the interior passageway 42.

Figure 8:
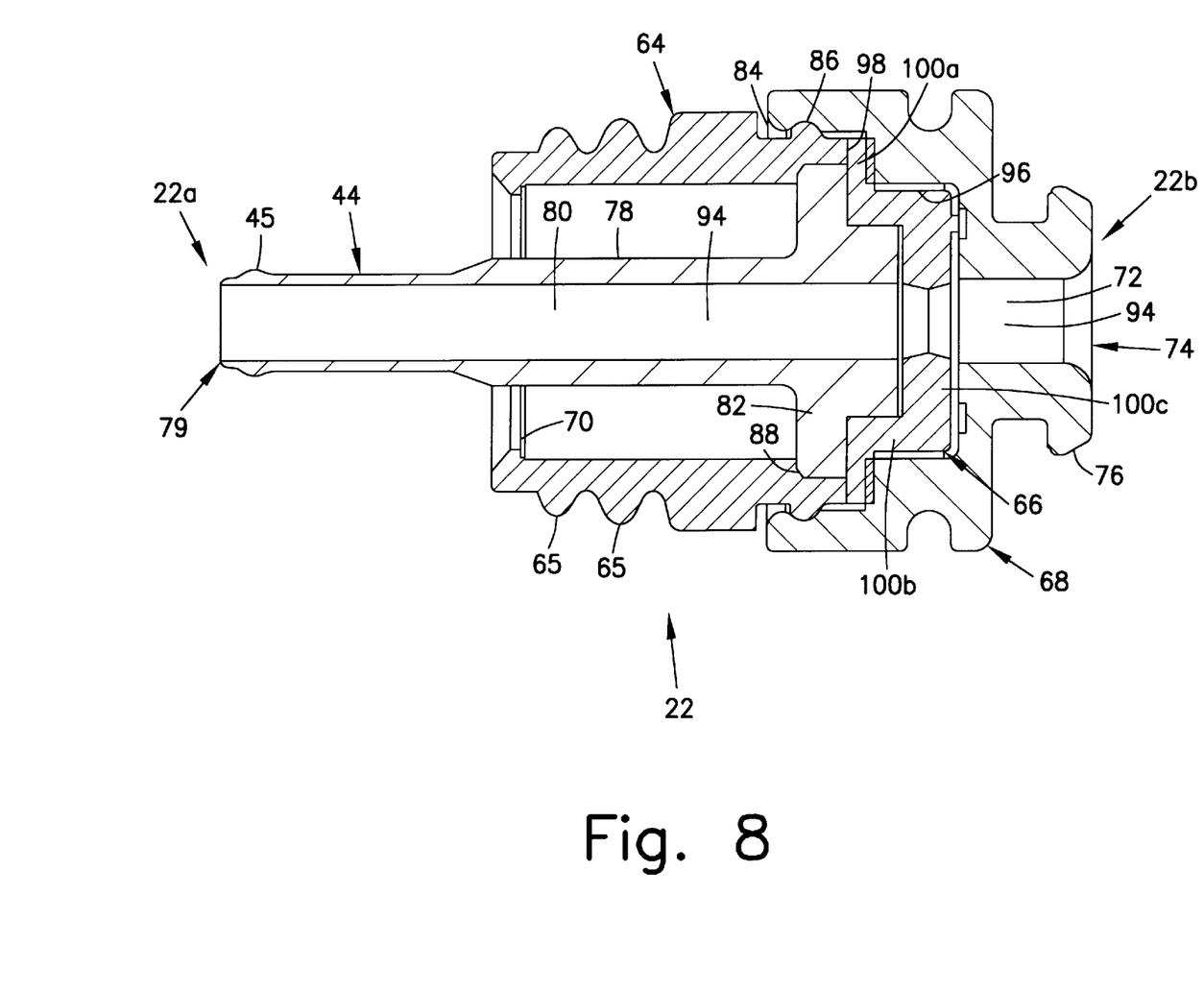
FIG. 8 is a longitudinal cross-sectional view of another embodiment of a shuttle housing of the invention.

Optionally, shuttle tube 44 may also be formed with a barb 45 at its distal end. As illustrated in FIG. 8, the proximal end of barb 45 flares outward and then tapers inwardly towards its distal end. The barb 45 can hasten closure of the sheath valve 28 when the shuttle tube 44 is withdrawn from the sheath valve.

Shuttle valve 66 preferably is located at the proximal end of shuttle tube 44, secured between shuttle tube 44 and cap 68. The shuttle valve 66 most preferably is essentially an O-ring valve that has an inner diameter that is sized to be slightly smaller than the outer diameter of a catheter that will be inserted through it. The opening in the shuttle valve 66 is axially aligned and in fluid communication with the entrance port 74 and interior passageway 80 of shuttle tube 44. Preferably, valve 66 has a "top hat"-type construction, whereby the valve has an axially extending portion 96 emanating from the O-ring section and leading to an outer radial section 98. Thus, valve 66 preferably is constructed to be secured in three different locations: at position 100a, the radial portion 98 is secured between the housing 64, shuttle tube 44, and cap 68; at position 100b, the axial portion 96 is secured between shuttle tube 44 and cap 68; at position 100c, the O-ring portion is secured between shuttle tube 44 and cap 68. Valve 66 preferably is made from an elastomeric material, such as a silicone elastomer, having a durometer between 20 and 80.

When elastomeric valves with inner diameters are compressed, their inner diameters have a tendency to decrease due to the compression. A "top-hat" design of the valve, however, can allow the valve 66 to be compressed between the cap 68 and shuttle tube 44 without significantly reducing the inner diameter of the valve.

As illustrated in FIG. 3, the shuttle body 64, shuttle cap 68, shuttle tube 44 and shuttle valve 66 are secured in place by a snap-fit engagement between shuttle cap rim 84 and rib 86. Prior to engagement, the distal side of shoulder 82 of the shuttle tube 44 is held against a mating shoulder 88 located on the interior surface of shuttle body 64. In addition, the distal side of the shuttle valve 66 is held against the proximal side of the shoulder 82 on the shuttle tube 44. When the shuttle cap rim 84 snap-fittingly engages rib 86, the shuttle cap 68 encapsulates the shuttle valve 66 and shuttle tube 44 and presses them together against the mating shoulder 88 of the shuttle body 64, thus sealing them in place.

The passageway 80 of the shuttle tube 44, the opening in the shuttle valve 66, and the passageway 72 of the shuttle cap 68 are axially aligned and in fluid communication with each other. Together they form a shuttle lumen 94.

Figure 9:
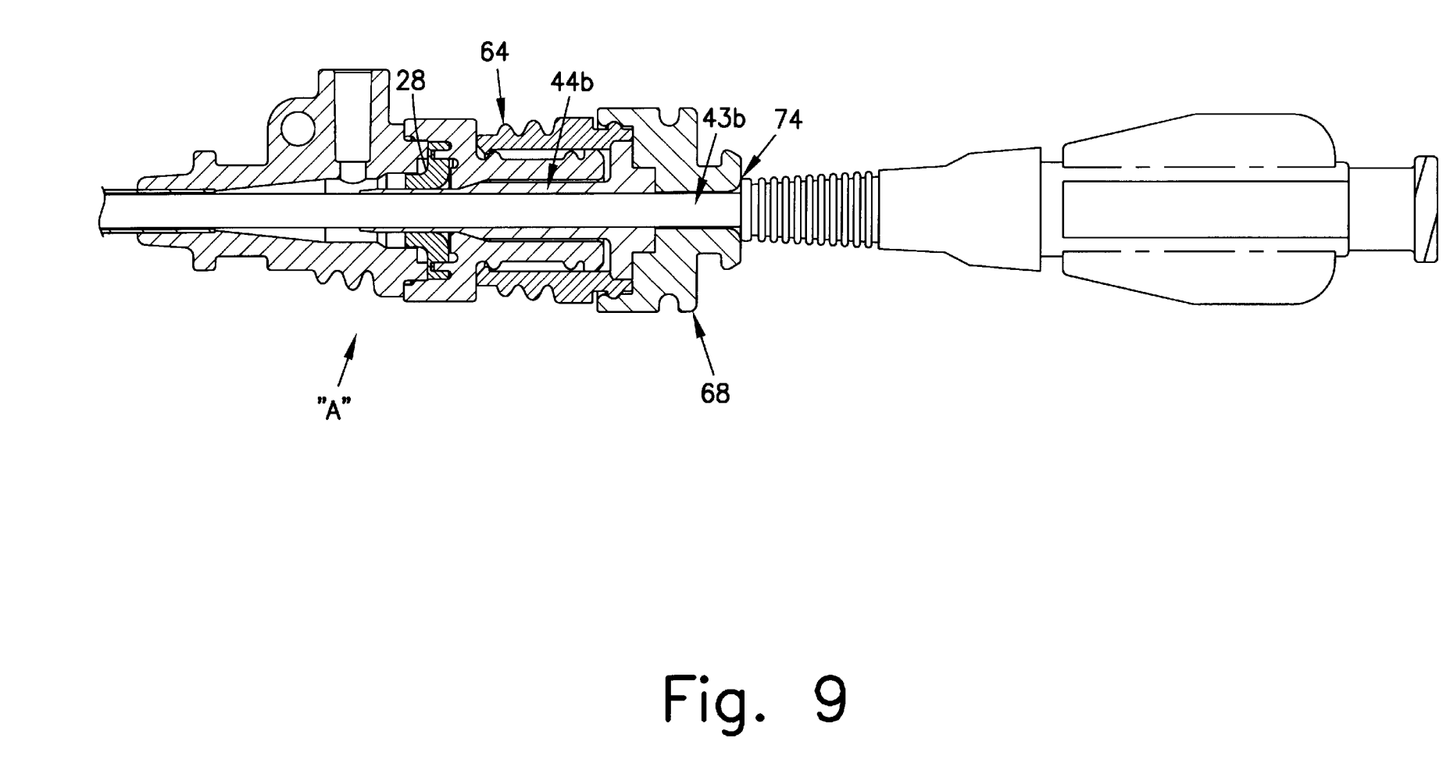
FIG. 9 is a longitudinal cross-sectional view of a catheter introducer of the invention, applying a fluid bearing seal to a catheter inserted therethrough.

As an alternative to using the washer valve 66 to provide hemostasis when the sheath valve 28 is biased open, a fluid bearing may be used. As illustrated in FIG. 9, the fluid bearing is formed by the interaction the shuttle tube 44b and a catheter 43b that is inserted through the introducer. The interior passageway of the shuttle tube 44b has a diameter that is slightly larger than the outer diameter of catheter 43b, thus creating a gap. When the catheter is inserted into the introducer and shuttle tube 44b has biased the sheath valve 28 open, blood flows into the gap. The gap is sufficiently small so that a sufficiently high resistance to flow is placed on the blood to prevent it from exiting the entrance port 74 of the shuttle cap 68; at the same time, the presence of small amounts of blood in the gap significantly reduces the friction caused by the movement of the catheter 43b relative to the interior passageway of the shuttle tube 44b. Thus, a fluid bearing is created. The fluid bearing gap width can be selected in accordance with the particular details of the device dimensions, so that blood is prevented from exiting the entrance port of shuttle cap 68. For a shuttle tube length of about 0.8 inches, a fluid bearing gap width less than about 0.002 inches is preferred. As illustrated in FIG. 9, shuttle tube 44b is positioned between the shuttle body 64 and the shuttle cap 68 by a snap-fit engagement.

Figure 10:
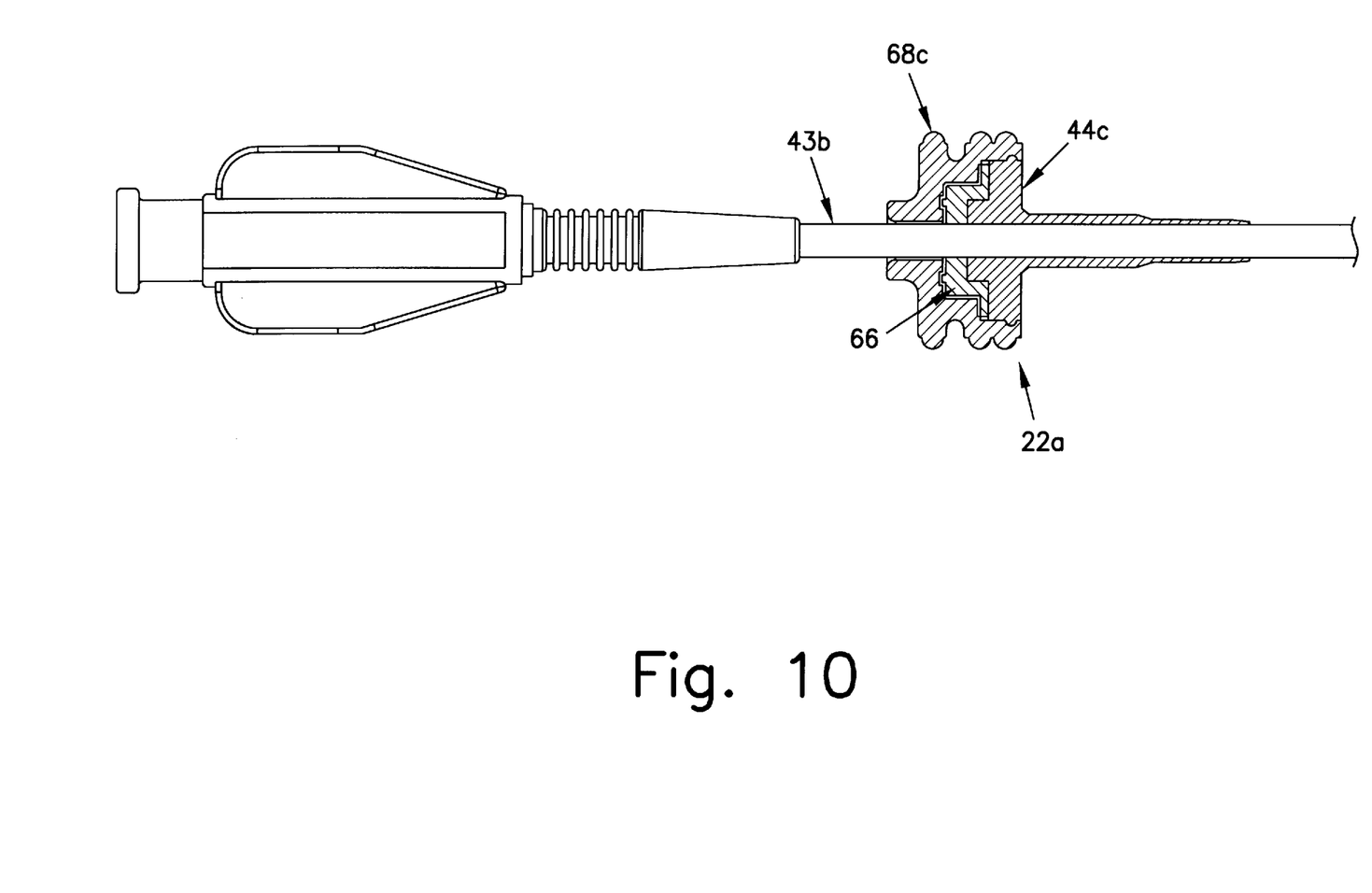
FIG. 10 is a longitudinal cross-sectional view of another embodiment of a shuttle housing of the invention having a catheter inserted therethrough.

An alternative embodiment of the device to the invention may comprise a single housing mounted on the shaft of a catheter or other elongated member as shown in FIG. 10. The shuttle housing 22a is similar to the shuttle housing 22 described in FIG. 3 in that a shuttle valve 66 is held fixedly between a shuttle tube 44c and a shuttle cap 68c. A shuttle body 64 of FIG. 3 is no longer necessary because the shuttle housing 22a of FIG. 10 need not attach to an introducer sheath, but floats unattached on the shaft of a catheter 43b or other elongated member. When reduced frictional drag is desired during a procedure, the shuttle housing 22a may be slid distally along the catheter or elongated member and introduced into the valve mechanism of an introducer sheath or Y-adaptor that is up to that point creating a hemostatic seal around the catheter or elongated member. In this way hemostatis around the perimeter of the shuttle housing is maintained by the valve mechanism of the introducer sheath or Y-adaptor, and hemostatis around the catheter or elongated member is maintained by the shuttle housing, particularly at the shuttle valve 66. As with previously described embodiments of the invention, an alternative to using the shuttle valve 66 to provide hemostatis around the catheter or elongated member is to use a fluid bearing as described in FIG. 9.

Alternative medical insertion devices that can be constructed according to the invention are Y- and tri-adapters. A preferred Y-adapter of the invention is illustrated in FIG. 5.

Instead of a washer valve, the device preferably includes a Tuohy-Borst valve 69b, which can seal around devices of varying diameter. In lieu of using a Tuohy-Borst valve, a duckbill valve or slit valve, having any suitable construction known in the art, may also be used. In general, a washer valve is not preferred in this embodiment, since elongated members of different diameters may be used in a single procedure in this embodiment of the invention.

Figure 5:
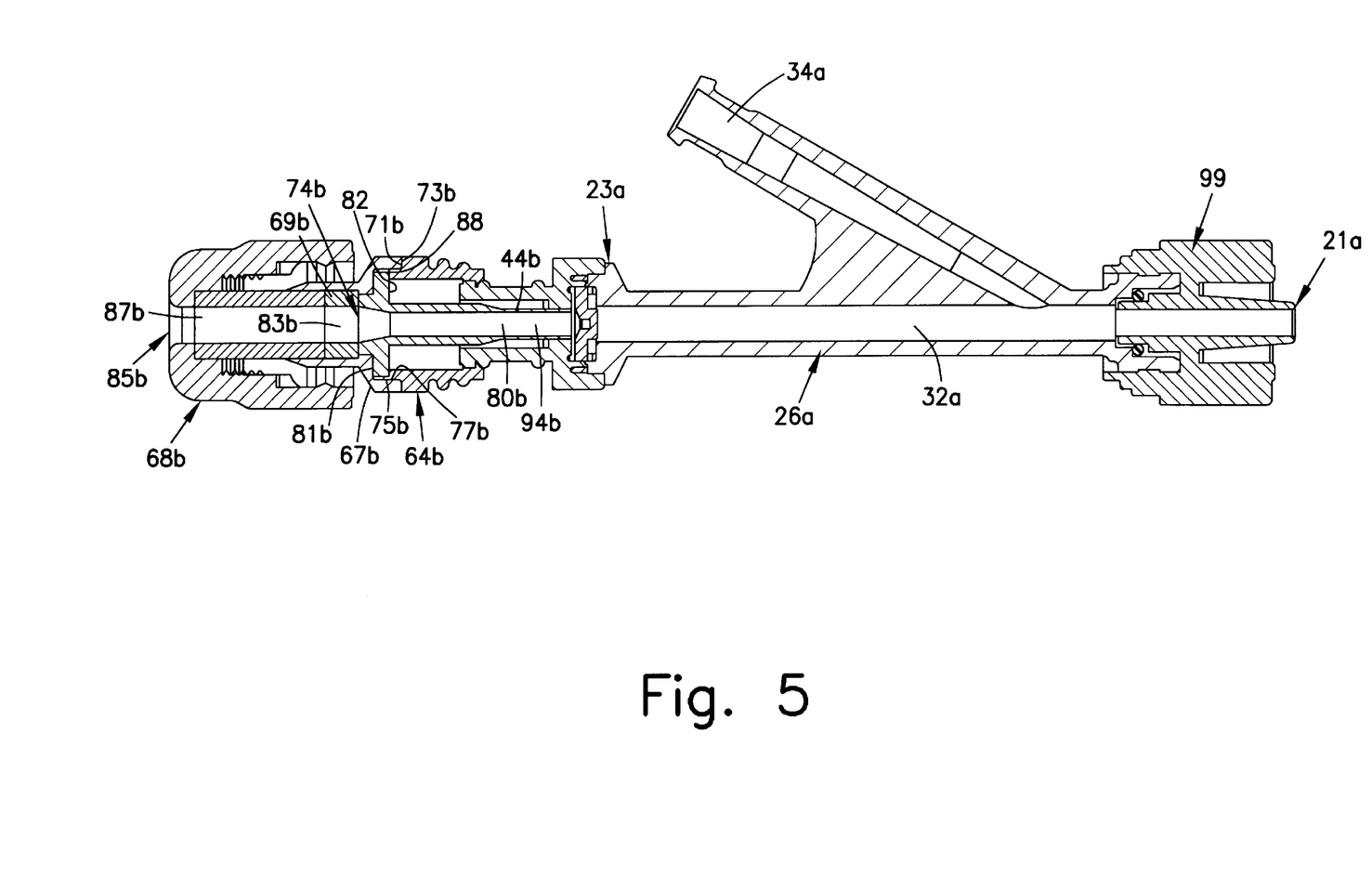
FIG. 5 is a longitudinal cross-sectional view of a Y-adapter of the invention in the unbiased position.

As shown in FIG. 5, the interior passageway 80b of shuttle tube 44b has a diameter that tapers outwardly from the distal end of the shuttle tube 44b to the entrance port 74b of the shuttle tube. The Tuohy-Borst valve cap assembly 68b preferably has a shoulder 67b that attaches to the proximal end of the shuttle body 64b; the shuttle body 64b is constructed similar to the shuttle housing 64 described above, but preferably does not have a rib 86 to secure the shuttle cap 68 to the shuttle body.

Preferably, the shoulder 67b is secured to the proximal end of the shuttle body 64b by ultrasonic welding. Most preferably, face 71b of shoulder 67b abuts face 73b of the shuttle body 64b. Face 75b of shoulder 67b abuts face 77b of shuttle body 64b. Face 81b of shoulder 67b abuts the proximal face of the shuttle body 64b and the proximal face of shoulder 82 of shuttle tube 44b. The distal face of shoulder 82 abuts the mating shoulder 88 on the shuttle body 64b.

Preferably located within the Tuohy-Borst valve cap assembly 68b is a compressible and expandable O-ring valve 69b. Most preferably, the O-ring valve 69b is located adjacent to the proximal end of the shuttle tube 44b. The interior 83b of the O-ring valve is in fluid communication with the entrance port 74b of the shuttle tube 44b.

The Tuohy-Borst valve cap assembly 68b comprises an entrance port 85b and interior passageway 87b that is large enough to accommodate the elongated member to be inserted through the Y-adapter. The entrance port 85b and interior passageway 87b are in fluid communication with the interior 83b of O-ring valve 69b; thus, the entrance port 85b and interior passageway 87b are in fluid communication with the shuttle lumen 94b. For tri-adapters, the structure of the Tuohy-Borst valve assembly is the same.

As shown in FIG. 5, Y-adapter stem 26a has an interior passageway 32a that extends from distal end 21a to the proximal end 23a of the Y-adapter stem 26a. The interior passageway 32a has a diameter that remains generally constant the entire length of the Y-adapter stem 26a. The Y-adapter distal connector 99 typically is used to connect the Y-adapter to the hub of a guide catheter, or similar device.

A side passageway 34a extends away from the Y-adapter interior passageway 32a. The side passageway 34a is in fluid communication with the interior passageway 32a, and thus provides access to the vascular system for purposes of injecting medication, saline, or contrast media.

Tri-adapters of the invention are similar to the Y-adapter, with the exception that an additional passageway containing the same valve assembly as in the Y-adapter is included.

Returning to FIG. 1, the shuttle housing 22 is coupled to the sheath housing 20, with rim 70 extending over annular collar 50 and snap-fittingly engaging the outer surface 92 of the sheath cap 30. The shuttle housing 22 may slide along the outer surface 92 from annular collar 50 to outer shoulder 47. Annular collar 50 prevents shuttle housing 22 from sliding off the proximal end of the sheath cap 30. Frictional forces between the rim 70 and outer surface 92 are sufficient to prevent the shuttle housing 22 from inadvertently sliding along the outer surface without the application of an external force. In a preferred embodiment, the annular collar 50 is sized so that once the rim 70 has snap-fittingly engaged the sheath cap 30, the shuttle housing 22 may not be readily removed from the sheath housing 20 without causing destructive effects on the device.

In an alternative embodiment, the shuttle housing 22 may be removably attached to the sheath housing 20. Here, the annular collar 50 is sized so that the rim 70 of the shuttle body 64 may extend over the annular collar 50 so as to snap-fittingly engage the sheath housing 20, but is small enough to allow the rim 70 to be taken off the collar 50 by application of external force.

Figure 6:
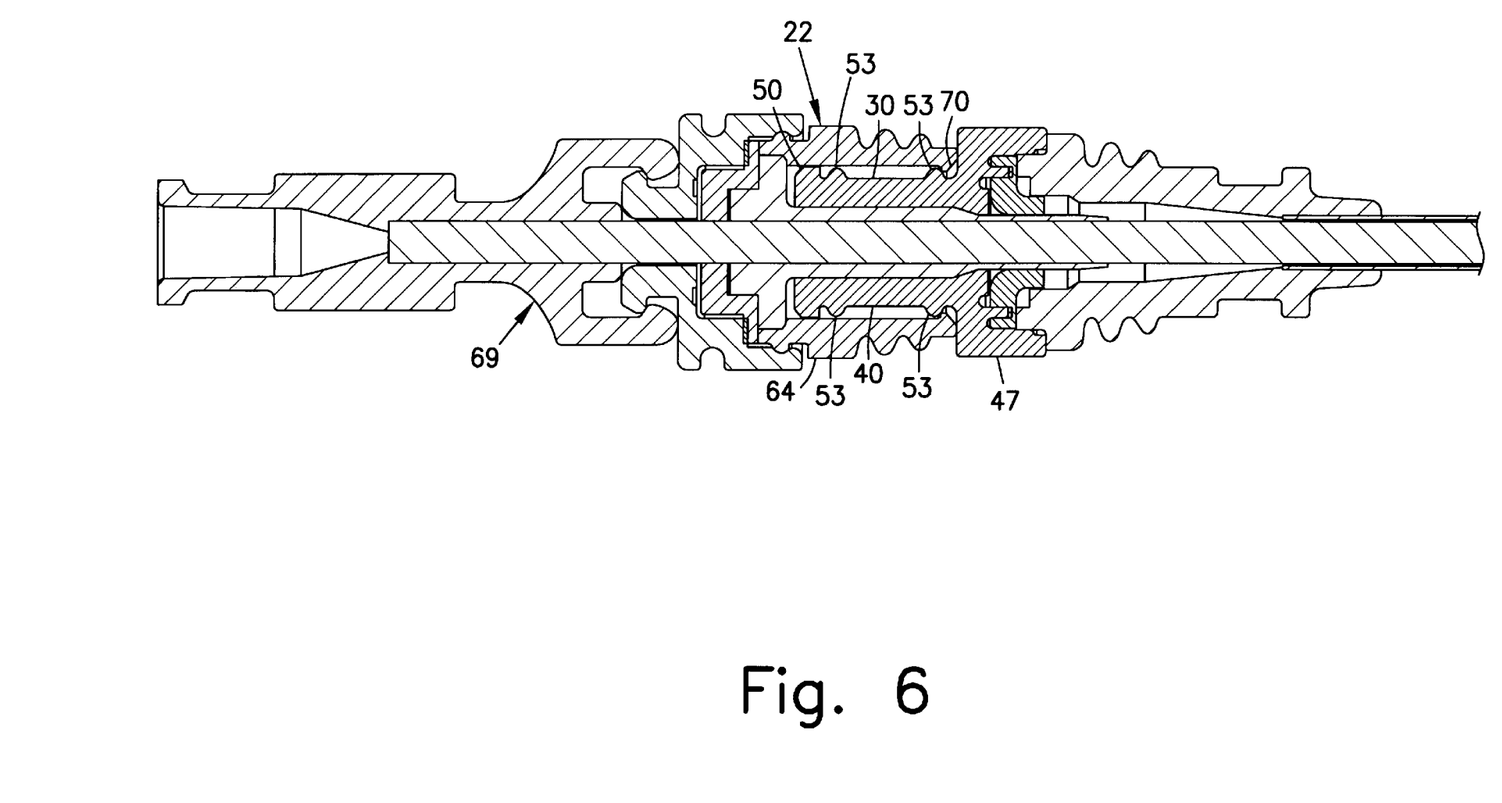
FIG. 6 is a longitudinal cross-sectional view of a catheter introducer of the invention having a dilator attached to its proximal end.

Optionally, devices of the invention may be provided with a locking mechanism that secures the shuttle housing in either the biased or unbiased position, or both. The locking mechanism preferably comprises one or more snap-rings located on the sheath cap body. As illustrated in FIG. 6, the locking mechanism may comprise a pair of snap-rings 53 located near the proximal and distal ends of the sheath cap body 40 of the sheath cap 30. The distance between the proximal end of outer shoulder 47 and distal side of snap ring 53 is sized such that when the rim 70 is adjacent to the distal side of the snap ring 53, the most distal end of the shuttle body 64 abuts the proximal end of shoulder 47. Thus, when the rim 70 of the shuttle housing 22 engages the distal snap-ring 53, the rim 70 is secured in place. Proximal snap-ring 53 is located near the proximal end of sheath cap body 40, such that the rim 70 can engage between the snap-ring 53 and the sheath collar 50. Instead of a snap-ring arrangement, the locking mechanism may comprise a threaded lock, interference-fit lock, or any other suitable means for preventing undesired movement of the shuttle mechanism.

In a typical procedure utilizing the catheter introducer system of the invention, a user first accesses an artery by inserting a needle therein. A guide wire is then inserted inside the needle until it is inside the artery. The user then removes the needle, which leaves only the guide wire in the artery. Next, the physician inserts a dilator through the introducer device until the dilator is in the sheath tube 24, and then the physician slides the sheath tube 24 and dilator over the guide wire until the distal ends of the sheath tube 24 and dilator are inside the artery. The sheath hub 26 is located just outside the body. The dilator is then removed followed by the guide wire.

At this point, blood can flow into the catheter introducer system. The sheath valve 28 is closed and maintains hemostasis. Although the guide wire extends through the sheath valve 28 prior to its removal, the valve 28 seals around the guide wire, which does not create an opening in valve 28 large enough to permit blood to pass into the shuttle lumen 94.

After the sheath tube 24 is in place, the user places a catheter over a second guide wire and inserts the catheter and guide wire into the entrance port 74 of the shuttle cap 68 and guides them through the shuttle valve 66 and shuttle tube 44, until they reach the sheath valve 28. The user then advances the catheter and guide wire through the sheath valve 28. The sheath valve 28 provides hemostasis at this point by engaging the periphery of the catheter. Alternatively, if desired, prior to advancing the catheter through the sheath valve 28 the user could bias the shuttle tube 44 forward until it opens the sheath valve 28 and then push the catheter and guide wire through the opened sheath valve, as is discussed in more detail below.

When the user desires increased maneuverability of the catheter, the user may bias the shuttle housing 22 towards the sheath housing 20. The user may slide the shuttle housing 22 along the outer surface 92 of the sheath cap 30, such as by gripping the sheath ribs 89 on the sheath housing 20 (see FIG. 4) and the shuttle ribs 65 on the shuttle housing 22. Because the shuttle tube 44 is connected to the shuttle housing 22, the shuttle tube 44 also moves forward and biases the sheath valve 28 open so that the sheath valve no longer engages the periphery of the catheter. Consequently, the maneuverability of the catheter is increased. As shown in FIG. 4, the shuttle lumen 94 of the shuttle housing 22 is axially aligned with the sheath lumen 46 of the sheath housing 20. The shuttle lumen 94 is thus in fluid communication with sheath lumen 46 when the sheath valve 28 is open. When the shuttle housing 22 is biased forward fully, the rim 70 of the shuttle body 64 abuts outer shoulder 47 of sheath cap 30.

Figure 7:
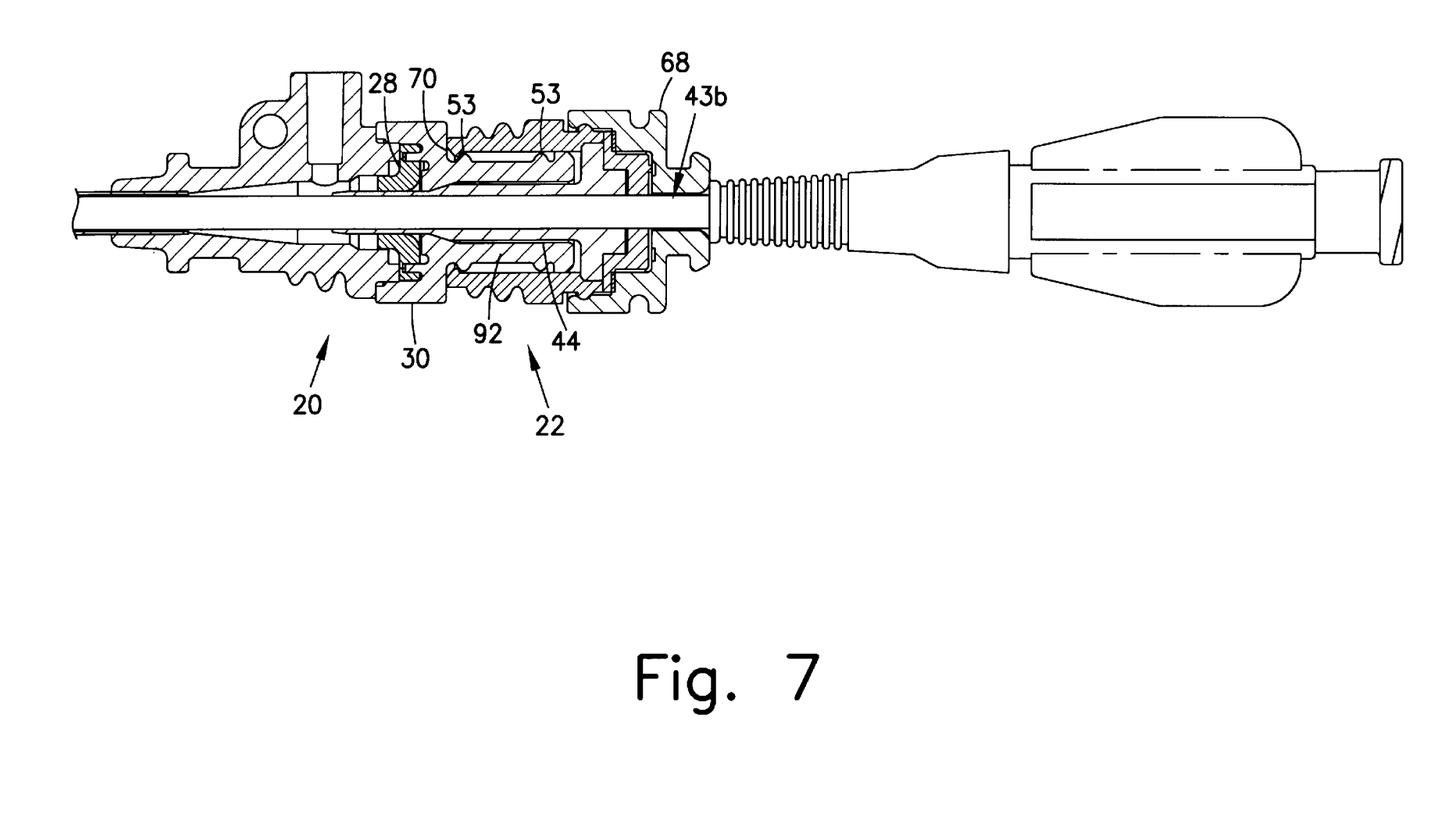
FIG. 7 is a longitudinal cross-sectional view of a catheter introducer of the invention having a catheter inserted therethrough.

When the sheath valve 28 is opened, as shown in FIG. 4, blood can flow through the sheath housing 20 into the shuttle housing 22. The sheath valve 28 provides hemostasis around the shuttle tube 44, and the shuttle valve 66 provides hemostasis around the catheter to prevent the loss of blood. Since the diameter of the shuttle valve 66 is only slightly smaller than the outer diameter of the catheter, the shuttle valve 66 is able to provide hemostasis without sacrificing maneuverability. FIG. 7 depicts a device similar to that shown in FIG. 4, having a catheter 43*b* inserted therethrough. The device of FIG. 7 also contains snap-rings 53 as a locking mechanism for rim 70.

A similar procedure can be used with interventional devices such as Y- or tri-adapters. However, a catheter or other elongated member does not necessarily have to be inserted through the device before the shuttle valve can provide hemostasis. In these types of devices, the shuttle valve may comprise a Tuohy-Borst valve, duckbill valve or slit valve. The opening in a Tuohy-Borst valve may be manually changed such that the opening is completely shut and thus provide hemostasis, even without a catheter. A duckbill valve or slit valve usually comprises a slit that remains closed until something is inserted through it and thus can provide hemostasis even when a catheter is not present. In addition, if the user withdraws an elongated member such as a balloon catheter out of the device, the user may withdraw the elongated member even if the sheath valve 28 is biased open and hemostasis will still be maintained. In such an instance, if the shuttle valve 66 is a Tuohy-Borst valve, the opening may be manually closed upon withdrawal of the catheter to maintain hemostasis. If the shuttle valve is a duckbill valve, the opening automatically closes upon withdrawal of the elongated member and hemostasis is maintained.

It should be appreciated that the foregoing is by way of example only, and that alterations or modifications may be made within the scope of the invention.

What is claimed is:

1. A medical insertion device for introducing an elongated member into a vascular system and facilitating maneuverability of the elongated member through the vascular system while providing hemostasis, the device comprising:

a housing having an interior lumen extending therethrough;

a sheath tube attached to a distal end of the housing, the sheath tube having a distal end adapted for insertion into the vascular system;

a first elastomeric valve secured within the interior lumen of the housing and having an openable slit therein;

a shuttle tube having proximal and distal ends and an interior passageway, the interior passageway being in fluid communication with the interior lumen of the housing, the shuttle tube being capable of biasing the first elastomeric valve open; and means for maintaining hemostasis when the shuttle tube biases the first elastomeric valve open, the means for maintaining hemostasis being coupled to the shuttle tube, wherein the means for maintaining hemostasis comprises a Tuohy-Borst valve having an opening that is changeable in size so as to engage an outer diameter of the elongated member, the elongated member being inserted through the device.

2. A medical insertion device for introducing an elongated member into a vascular system and facilitating maneuverability of the elongated member through the vascular system while providing hemostasis, the device comprising:

a housing having an interior lumen extending therethrough;

a sheath tube attached to a distal end of the housing, the sheath tube having a distal end adapted for insertion into the vascular system;

a first elastomeric valve secured within the interior lumen of the housing and having an openable slit therein;

a shuttle tube having proximal and distal ends and an interior passageway, the interior passageway being in fluid communication with the interior lumen of the housing, the shuttle tube being capable of biasing the first elastomeric valve open; and means for maintaining hemostasis when the shuttle tube biases the first elastomeric valve open, the means for maintaining hemostasis being coupled to the shuttle tube, wherein the means for maintaining hemostasis comprises a fluid bearing.

3. A medical insertion device that introduces an elongated member into a vascular system and facilitates maneuverability of the elongated member through the vascular system while providing hemostasis, the device comprising:

a first housing having proximal and distal ends and an interior lumen extending therethrough;

a sheath tube attached to the distal end of the first housing, the sheath tube having a distal end adapted for insertion into the vascular system;

an elastomeric valve secured within the first housing and having an openable slit through the valve;

a second housing having proximal and distal ends, the second housing being connectable to the first housing and being adapted to move reciprocally relative to the first housing, the second housing having an entrance port located at its proximal end and an interior lumen extending therethrough, in fluid communication with the entrance port;

a shuttle tube having proximal and distal ends and an interior passageway and being secured within the second housing, the distal end of the shuttle tube selectively biasing the elastomeric valve open so that the interior passageway is in fluid communication with the interior lumen of the first housing; and means for providing hemostasis secured within the interior lumen of the second housing and located proximally of the shuttle tube, such that when the second housing is moved toward the distal end of the first housing, the shuttle tube biases the elastomeric valve open and the means for providing hemostasis provides hemostasis, wherein the valve comprises a Tuohy-Borst valve having an opening that is in fluid communication with the interior passageway of the shuttle tube and the entrance port, the opening being changeable in size so as to engage an outer diameter of the elongated member, the elongated member being inserted through the device.

4. A medical insertion device that introduces an elongated member into a vascular system and facilitates maneuverability of the elongated member through the vascular system while providing hemostasis, the device comprising:

a first housing having proximal and distal ends and an interior lumen extending therethrough;

a sheath tube attached to the distal end of the first housing, the sheath tube having a distal end adapted for insertion into the vascular system;

an elastomeric valve secured within the first housing and having an openable slit through the valve;

a second housing having proximal and distal ends, the second housing being connectable to the first housing and being adapted to move reciprocally relative to the first housing, the second housing having an entrance port located at its proximal end and an interior lumen extending therethrough, in fluid communication with the entrance port;

a shuttle tube having proximal and distal ends and an interior passageway and being secured within the second housing, the distal end of the shuttle tube selectively biasing the elastomeric valve open so that the interior passageway is in fluid communication with the interior lumen of the first housing; and means for providing hemostasis secured within the interior lumen of the second housing and located proximally of the shuttle tube, such that when the second housing is moved toward the distal end of the first housing, the shuttle tube biases the elastomeric valve open and the means for providing hemostasis provides hemostasis, wherein the means for providing hemostasis comprises a fluid bearing.

5. A medical insertion device that introduces an elongated member into a vascular system and facilitates maneuverability of the elongated member through the vascular system while providing hemostasis, the device comprising:

a first housing having proximal and distal ends and an interior lumen extending therethrough;

a sheath tube attached to the distal end of the first housing, the sheath tube having a distal end adapted for insertion into the vascular system;

an elastomeric valve secured within the first housing and having an openable slit through the valve;

a second housing having proximal and distal ends, the second housing being connectable to the first housing and being adapted to move reciprocally relative to the first housing, the second housing having an entrance port located at its proximal end and an interior lumen extending therethrough, in fluid communication with the entrance port;

a shuttle tube having proximal and distal ends and an interior passageway and being secured within the second housing, the distal end of the shuttle tube selectively biasing the elastomeric valve open so that the interior passageway is in fluid communication with the interior lumen of the first housing; and means for providing hemostasis secured within the interior lumen of the second housing and located proximally of the shuttle tube, such that when the second housing is moved toward the distal end of the first housing, the shuttle tube biases the elastomeric valve open and the means for providing hemostasis provides hemostasis, wherein the device further comprises a locking mechanism disposed on at least one of the first housing and the second housing, the locking mechanism being selectively operable to restrict movement of the second housing relative to the first.

6. A medical insertion device that introduces an elongated member into a vascular system and facilitates maneuverability of the elongated member through the vascular system while providing hemostasis, the device comprising:

a sheath housing comprising a sheath hub, a sheath cap, and a sheath valve, the sheath hub being secured to the sheath cap such that an interior lumen is formed within, the sheath valve being secured in the interior lumen and having an openable slit extending through the valve;

a sheath tube attached to a distal end of the sheath housing, the sheath tube having a distal end adapted for insertion into the vascular system;

a shuttle housing that is connectable to the sheath housing and adapted to move relative to the sheath housing, the shuttle housing having proximal and distal ends and comprising a shuttle body and shuttle cap, the shuttle body having proximal and distal ends, the shuttle cap having proximal and distal ends and being secured to the proximal end of the shuttle body, the shuttle body and shuttle cap forming a hollow interior when secured together;

an entrance port located at the proximal end of the shuttle housing, a shuttle tube having proximal and distal ends and an interior passageway and being secured within the hollow interior of the shuttle housing, the distal end of the shuttle tube selectively biasing the elastomeric valve open so that the interior passageway is in fluid communication with the interior lumen of the sheath housing; and a shuttle valve secured within the hollow interior of the shuttle housing and located proximally of the shuttle tube such that when the shuttle housing movably engages the sheath housing, the shuttle tube biases the sheath valve open and the shuttle valve provides hemostasis, wherein the shuttle valve comprises a Tuohy-Borst valve having an opening that is changeable depending upon the outer diameter of the elongated member inserted through the device.

7. A medical insertion device that introduces an elongated member into a vascular system and facilitates maneuverability of the elongated member through the vascular system while providing hemostasis, the device comprising:

a sheath housing comprising a sheath hub, a sheath cap, and a sheath valve, the sheath hub being secured to the sheath cap such that an interior lumen is formed within, the sheath valve being secured in the interior lumen and having an openable slit extending through the valve;

a sheath tube attached to a distal end of the sheath housing, the sheath tube having a distal end adapted for insertion into the vascular system;

a shuttle housing that is connectable to the sheath housing and adapted to move relative to the sheath housing, the shuttle housing having proximal and distal ends and comprising a shuttle body and shuttle cap, the shuttle body having proximal and distal ends, the shuttle cap having proximal and distal ends and being secured to the proximal end of the shuttle body, the shuttle body and shuttle cap forming a hollow interior when secured together;

an entrance port located at the proximal end of the shuttle housing, a shuttle tube having proximal and distal ends and an interior passageway and being secured within the hollow interior of the shuttle housing, the distal end of the shuttle tube selectively biasing the elastomeric valve open so that the interior passageway is in fluid communication with the interior lumen of the sheath housing; and a shuttle valve secured within the hollow interior of the shuttle housing and located proximally of the shuttle tube such that when the shuttle housing movably engages the sheath housing, the shuttle tube biases the sheath valve open and the shuttle valve provides hemostasis, wherein the device further comprises a locking mechanism disposed on at least one of the first housing and the second housing, the locking mechanism being selectively operable to restrict movement of the second housing relative to the first.

8. A medical insertion device that assists introduction of an elongated member into a vascular system and facilitates maneuverability of the elongated member through the vascular system while providing hemostasis, the device comprising:

a housing comprising proximal and distal ends and having an interior lumen;

a shuttle tube secured within the interior lumen and having an interior passageway;

a means for providing hemostasis located in the interior lumen, the means for providing hemostasis including a fluid bearing;

wherein the device is used to bias open a valve in a second medical insertion device so as to facilitate maneuverability of the elongated member through the second medical insertion device and provide hemostasis.

9. A method for introducing an elongated member into a vascular system and facilitating the maneuverability of the elongated member through the vascular system while maintaining hemostasis, the method comprising the steps of:

(a) accessing a vascular system of a patient with a needle;

(b) inserting a first guide wire into the needle and into the vascular system;

(c) withdrawing the needle from the vascular system, leaving the guide wire in the vascular system;

(d) placing a medical insertion device over the guide wire and sliding a distal end of the device over the guide wire until the distal end of the device is in the vascular system, wherein the device comprises:

(I) a housing having proximal and distal ends and an entrance port and an interior lumen extending therethrough;

(ii) a sheath tube attached to the distal end of the housing and being inserted into the vascular system;

(iii) an elastomeric valve secured within the interior lumen of the housing and having an openable slit therein;

(iv) a shuttle tube having proximal and distal ends and an interior passageway, the interior passageway being in fluid communication with the interior lumen of the housing, the shuttle tube being capable of biasing the elastomeric valve open, and (v) means for providing hemostasis;

(e) withdrawing the first guide wire;

(f) placing the elongated member over a second guide wire and inserting the elongated member and second guide wire into the entrance port of the housing and guiding them through the device and into the vascular system; and (g) biasing the shuttle tube forward so that it opens the slit in the elastomeric valve.

10. The method according to claim 9, wherein the method further comprises biasing the shuttle tube away from the sheath valve, thus causing the slit in the elastomeric valve to close around the elongated member and guide wire.

11. A method for introducing an elongated member into a vascular system and facilitating the maneuverability of the elongated member through the vascular system while maintaining hemostasis, the method comprising:

(a) accessing a vascular system of a patient;

(b) providing a medical insertion device in fluid communication with the vascular system, the medical insertion device including a valve assembly comprising:

(i) a housing having proximal and distal ends and an entrance port and an interior lumen extending therethrough;

(ii) a first elastomeric valve secured within the interior lumen of the housing and having an openable slit therein;

(iii) a shuttle tube having proximal and distal ends and an interior passageway, the interior passageway being in fluid communication with the interior lumen of the housing, the shuttle tube being capable of biasing the first elastomeric valve open; and (iv) means for providing hemostasis;

(c) inserting the elongated member into the entrance port of the housing and guiding it through the device; and (d) biasing the shuttle tube forward so that it opens the slit in the first elastomeric valve.

12. The method according to claim 11, wherein the means for providing hemostasis includes an opening having an inner diameter that is slightly smaller than an outer diameter of the elongated member.

13. The method according to claim 12, wherein the means for providing hemostasis comprises an O-ring valve.

14. The method according to claim 11, wherein the shuttle tube has an outer surface including a series of alternating flattened and curved surfaces along a longitudinal axis.

15. The method according to claim 11, wherein the shuttle tube includes a tapered distal tip.

16. The method according to claim 11, wherein the insertion device is formed as a y-adapter having first and second prongs, one of the first and second prongs including the valve assembly.

17. The method according to claim 11, wherein the means for providing hemostasis comprises a second elastomeric valve.

* * * * *